United States Patent [19]
Palmer et al.

[11] Patent Number: 6,139,817
[45] Date of Patent: Oct. 31, 2000

[54] METHOD FOR DETERMINING GENE ESSENTIALITY IN A PATHOGEN

[75] Inventors: Leslie M. Palmer, Malvern, Pa.; Julie M. Pratt, Verona, Italy; Martin M. Rosenberg, Royersford, Pa.

[73] Assignee: Smithkline Beecham Corporation, Philadelphia, Pa.

[21] Appl. No.: 09/010,523

[22] Filed: Jan. 21, 1998

Related U.S. Application Data

[63] Continuation-in-part of application No. 08/949,564, Oct. 14, 1997, abandoned.
[60] Provisional application No. 60/028,416, Oct. 15, 1996, and provisional application No. 60/031,161, Nov. 18, 1996.

[51] Int. Cl.[7] .......................... A61K 49/00; C12N 15/63; C12Q 1/68
[52] U.S. Cl. .................. 424/9.1; 424/93.2; 424/93.6; 424/9.2; 435/6; 435/7.1; 435/7.2; 435/29; 435/320.1; 435/252.3; 435/252.31; 435/252.33; 435/252.34; 435/252.35; 536/23.1; 536/24.1
[58] Field of Search ................................. 435/6, 7.1, 7.2, 435/29, 320.1, 252.3, 252.31, 252.33, 252.34, 252.35; 424/9, 93.2, 93.6

[56] References Cited

U.S. PATENT DOCUMENTS 5,756,305  5/1998  Timberlake et al. .................. 435/34

FOREIGN PATENT DOCUMENTS

| | | |
|---|---|---|
| 0 467 349 | 1/1992 | European Pat. Off. . |
| 0 628 635 | 12/1994 | European Pat. Off. . |
| WO 91/07087 | 5/1991 | WIPO . |
| WO 91/17271 | 11/1991 | WIPO . |
| WO 92/01806 | 2/1992 | WIPO . |
| WO 95/29245 | 11/1995 | WIPO . |
| WO 95/30755 | 11/1995 | WIPO . |

OTHER PUBLICATIONS

Agius et al., Advances in Virus Research, vol. 44, pp. 357–379, 1994.
Harold M. Weintrob, "Antisense RNA and DNA", *Scientific American*, pp. 40–46 (Jan. 1990).
Hensel, et al., "Simultaneous Identification of Bacterial Virulence Genes By Negative Selection", *Science*, vol. 269, pp. 400–403, (1995).
Guerrier–Takada, et al, "Artificial Regulation of Gene Expression in *Escherichia coli* by Rnase P", *Proc. Natl Acad. Sci. USA*, vol. 92:, pp 11115–11119, (Nov. 1995).
Lee, et al., *J. Infect. Dis.* vol. 156; 741, (1987).
Fields, et al., *Proc. Natl. Acad. Sci.*, vol. 83: 5189, (1986).
Finlay, et al., *Mol. Microbiol.*, vol. 2: 757, (1988).
Miller, et al., *Infect. Immun.*, vol. 57: 2758, (1989).
Bolker, et al., *Mol. Gen. Genet.*, vol. 248: 547–552, (1994).
Augustin, et al., *Eur. J. Biochem.*, vol. 204: 1149–1154, (1992).
Slauch, et al., *Methods in Enzymology*, vol. 235: 481–492, (1994).

*Primary Examiner*—David Guzo
*Attorney, Agent, or Firm*—Edward R. Gimmi; William T. King; Charles M. Kinzig

[57] ABSTRACT

The present invention provides a method for determining pathogen sensitivity to varying levels of reduction of a gene product using an expression vector system having a promoter that is essentially off in vitro and turns on selectively during the infection process in vivo. Genes and gene products identified by this method as essential to growth of infection of a selected pathogen are also provided. In addition, therapeutic compositions designed to target genes identified by this method are provided.

26 Claims, No Drawings

SEQUENCE LISTING

<160> NUMBER OF SEQ ID NOS: 1

<210> SEQ ID NO 1
<211> LENGTH: 281
<212> TYPE: DNA
<213> ORGANISM: Staphylococcus aureus

<400> SEQUENCE: 1

```
gatgcagaag cgatttacac gtacgaaggt acacatgaaa ttaatgcctt agtaattgga      60
cgcgctttga ctggagattc tgctttcgta taaatagcaa ataattatat gagatgcatt     120
aatttcacta aaaagactt attttaagca taagctttt tccttaaata agaggctaag      180
atgactgtca aagatactta attaatttta taaaatagca acgttattcc aattatctta     240
atggttatct tatcctcaac taaattggag gaatcactat g                         281
```

METHOD FOR DETERMINING GENE ESSENTIALITY IN A PATHOGEN

RELATED APPLICATIONS

This Application is a continuation-in-part of Ser. No. 08/949,564, filed Oct. 14, 1997, now abandoned, and claims the benefit of U.S. Provisional Applications Serial No. 60/028,416, filed Oct. 15, 1996, and Serial No. 60/031,161, filed Nov. 18, 1996.

FIELD OF THE INVENTION

The present invention provides a method for determining pathogen sensitivity to varying levels of reduction of expression of a gene product using an expression vector system having a promoter that is essentially "off" in vitro and turns "on" selectively during the infection process. Using this method, gene targets most sensitive to inhibition can be selected as molecular targets for the development of new therapies against selected pathogens.

BACKGROUND OF THE INVENTION

Identification, sequencing and characterization of genes is a major goal of modern scientific research. By identifying genes, determining their sequences and characterizing their biological function, it is possible to employ recombinant technology to produce large quantities of valuable gene products, e.g. proteins and peptides. Additionally, knowledge of gene sequences can provide a key to diagnosis, prognosis and treatment in a variety of disease states in plants and animals which are characterized by inappropriate expression and/or repression of selected genes or by the influence of external factors, e.g., carcinogens or teratogens, on gene function.

A variety of techniques have also been described for identifying particular gene sequences on the basis of their gene products. For example, see International Patent Application No. WO91/07087, published May 30, 1991. In addition, methods have been described for the amplification of desired sequences. For example, see International Patent Application No. WO91/17271, published Nov. 14, 1991.

Genes which are essential for the growth of an organism, however, have been difficult to identify in such a manner as to be easily recovered for future analysis. The most common methodology currently employed to identify essential genes is a multi-step process involving the generation of a conditionally lethal mutant library followed by the screening of duplicate members under the appropriate permissive and non-permissive conditions. Candidate mutants are then transformed with a second, genomic library and the desired genes isolated by complementation of the mutant phenotype. The complementing plasmid is recovered, subcloned, and then retested. However, this procedure comprises multiple subcloning steps to identify and recover the desired genes thus making it both labor intensive and time consuming.

A number of approaches for the isolation of pathogen virulence genes based upon transposon mutagenesis have been developed. These include screening for the loss of specific virulence-associated factors (Lee et al. *J. Infect. Dis.* 1987, 156:741), survival within macrophages (Fields et al. *Proc. Nat'l Acad. Sci.* 1986, 83:5189), and penetration of epithelial cells (Finlay et al. *Mol. Microbiol.* 1988, 2:757). However, these methods are restricted to certain stages of infection.

Transposon mutants have also been tested in live animal models of infection (Miller et al. *Infect. Immun.,* 1989, 57:2758; and Bolker et al., *Mol. Gen. Genet.,* 1994, 248:547–552). However, comprehensive screening of bacterial genes is not possible due to the inability to identify mutants with attenuated virulence within pools of mutagenized bacteria and thus the huge number of mutants would require individual screening.

Hensel et al. have developed an insertional mutagenesis system that uses transposons carrying unique DNA sequence tags for the isolation of bacterial virulence genes. *Science,* 1995, 269:400–403. In this system, termed signature-tagged mutagenesis, each transposon mutant is tagged with a different DNA sequence. This permits identification of bacteria recovered from hosts infected with a mixed population of mutants, as well as the selection of mutants with attenuated virulence. This method was used to identify virulence genes of *Salmonella typhimurium* in a murine model of typhoid fever. Further, Slauch et al. describe a method referred to as IVET technology which provides a means for identifying transcripts which are essentially absent in vitro, but are on throughout, or during, various phases of infection (*Methods in Enzymology* 1994, 235:481–492). However, these methods only provide information on the effect of the total absence or the specific up-regulation in vivo of the gene product in the organism.

Accordingly, there exists an unmet need for an efficient method of identifying varying levels of genes essential to the infectivity and growth of a pathogen.

SUMMARY OF THE INVENTION

In one aspect, the invention provides a method of identifying varying levels of a gene or genes that are essential to the infectivity and growth of a pathogen through the use of an expression vector system which uses a promoter that is "off" in vitro, and turns "on" selectively during a particular phase of the infection process of a pathogen.

An additional aspect of the invention provides an isolated gene which is essential to the infectivity and/or growth of a pathogen and is identified by the above method.

Yet another aspect of the invention is an isolated protein produced by expression of the gene sequence identified above. Such proteins are useful in the development of therapeutic and diagnostic compositions, or as targets for drug development.

Yet another aspect of the invention is to identify antibiotics, especially broad spectrum antibiotics, and particularly those that modulate the expression of these essential genes and/or activity of their gene products.

The invention provides a method of determining gene essentiality in a selected pathogen comprising: preparing a vector expression system comprising a promoter having on/off characteristics and a reporter gene; expressibly linking the promoter in the vector expression system with a ribozyme or antisense construct for the potential target gene; introducing the expression vector system containing the ribozyme or antisense construct into a selected pathogen; infecting at least one animal with the pathogen containing the expression vector system; determining gene expression levels of the target gene; and correlating target gene expression levels with progression of the infection in the animal to identify genes essential to growth of the selected pathogen.

The invention also provides method of determining gene essentiality in a selected pathogen comprising: preparing a vector expression system comprising a promoter of the potential target gene having on/off characteristics and a reporter gene; expressibly linking the target gene promoter in the vector expression system with a ribozyme or antisense construct for the potential target gene; introducing the expression vector system containing the ribozyme or antisense construct into a selected pathogen; infecting at least one animal with the pathogen containing the expression vector system; determining levels of mRNA of the target gene; and correlating levels of mRNA with progression of the infection in the animal to identify genes essential to growth of the selected pathogen.

Still further provided by the invention is a method of determining gene essentiality in a selected pathogen comprising: identifying a potential target gene; preparing a vector expression system comprising a promoter having on/off characteristics and a reporter gene; confirming that the on/off characteristics of the promoter in the vector expression system are preserved; replacing the reporter gene in the vector expression system with a ribozyme or antisense construct for the potential target gene; introducing the expression vector system containing the ribozyme or antisense construct into a selected pathogen; infecting at least one animal with the pathogen containing the expression vector system; determining levels of mRNA of the target gene; and correlating levels of mRNA with progression of the infection in the animal to identify genes essential to growth of the selected pathogen.

A method is also provided of determining gene essentiality in a selected pathogen comprising: preparing a vector expression system comprising a promoter having on/off characteristics and a reporter gene; expressibly linking the target gene promoter in the vector expression system with a ribozyme or antisense construct for the potential target gene; introducing the expression vector system containing the ribozyme or antisense construct into a selected pathogen; infecting at least one animal with the pathogen containing the expression vector system; determining levels of protein expressed by the target gene; and correlating levels of protein with progression of the infection in the animal to identify genes and gene products essential to growth of the selected pathogen.

Methods are also provided wherein the selected pathogen is selected from the group consisting of Streptococcus, *Streptococcus pneumoniae*, Staphylococcus, *Staphylococcus aureus*, Enterococcus, *Enterococcus faecalis*, Pseudomonas, *Pseudomonas aeruginosa*, Escherichia, and *Escherichia coli*.

Other methods are provided wherein the animal of the infecting step is selected from the group consisting of a rodent, a mouse, a rat, a rabbit, and a guinea pig.

The invention still further provides a kit comprising the vectors of the invention.

Provided by the invention are vector used in the methods of the invention, pathogen used in such methods.

Expression vectors comprising a promoter of a potential target gene having on/off characteristics and a reporter gene are also provided. Also provided are vectors comprising a gene promoter having on/off characteristics expressibly linked to a ribozyme or antisense construct for the potential target gene.

The invention also provides a pathogen comprising an expression vector comprising a promoter having on/off characteristics and a reporter gene, as well as a pathogen comprising a vector comprising a gene promoter having on/off characteristics expressibly linked to a ribozyme or antisense construct for the potential target gene. Animals comprising such pathogens are also provided by the invention.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

The biochemical basis of many pathogen resistance mechanisms to antimicrobials is now known. These mechanisms alone, or in concert, are responsible for the escalating problem of antimicrobial resistance seen in both hospital and community-acquired infections. The principle approach by researchers to overcome these problems has been to seek incremental improvements in existing drugs. While these approaches contribute somewhat to the fight against infection by such resistant pathogens, new approaches are needed.

Knowledge of genes or gene products essential to the growth of an organism can provide a key to the development of treatments of infectious pathogens. Gene knockout studies provide information on the effect of the total absence of a gene product. However, antimicrobial therapies can rarely achieve the complete abolition of activity of a given gene product. In addition, gene knockouts cannot be created (by simple insertion/deletion mutagenesis) if the gene products are essential to viability in vitro.

The present invention provides a method for determining pathogen sensitivity to varying levels of reduction of a gene product and is applicable to genes essential in vitro since reduction in levels of the gene product only occurs in vivo. The degree of mRNA reduction for a selected target can be monitored and correlated with the progression of the infection and/or viable counts recovered from infected tissue. Using this method, genes from a selected pathogen which are sensitive to inhibition in vivo can be identified and selected as targets for the development of new intervention therapies.

By "pathogen" it is meant any organism which is capable of infecting an animal or plant and replicating its nucleic acid sequences in the cells or tissue of the animal or plant. Such a pathogen is generally associated with a disease condition in the infected animal or plant. Such pathogens may include, but are not limited to, viruses, which replicate intra- or extracellularly, or other organisms such as bacteria, fungi or parasites, which generally infect tissues or the blood. Certain pathogens are known to exist in sequential and distinguishable stages of development, e.g., latent stages, infective stages, and stages which cause symptomatic diseases. In these different states, the pathogen is anticipated to rely upon different genes as essential for survival.

Preferred pathogens useful in the methods of the invention include, for example, Streptococcus, *Streptococcus pneumoniae*, Staphylococcus, *Staphylococcus aureus*, Enterococcus, *Enterococcus faecalis*, Pseudomonas, *Pseudomonas aeruginosa*, Escherichia, and *Escherichia coli*.

In this method, potential gene targets for antimicrobial therapy are first identified by either their essentiality for growth in vitro or their essentiality in infection. Essentiality for growth in vitro is determined for example by generation of conditional lethal mutants of a selected pathogen. The mutated gene can be identified by complementation with a genomic library prepared from the pathogen. Essentiality of a gene in the infection process is determined by generating individual gene deletions/knockouts or by using a random mutagenic approach followed by negative selection after cycling through an infection model such as signature-tagged mutagenesis (STM; Hensel et al., *Science,* 1995, 269:400–403).

Precedents for the existence of genes whose transcription is essentially off in vitro but on in vivo have been highlighted by the IVET technology (Slauch et al., *Methods in Enzymology,* 1994, 235:481–492) and RT-PCR analysis of total RNA isolated from infected tissue or in vitro grown cells. Using genome databases, primer pairs are designed to predicted transcripts of the selected pathogen and arrayed in microtiter dish format. Total RNA is isolated from an in vitro grown pathogen and RT-PCR performed with all the primer pairs. Similarly RT-PCR is performed with total RNA isolated at varying times from infections of the selected pathogen in a variety of appropriate animal models. Comparison of the PCR profiles which reflect the ratio of a given mRNA to internal standards such as rRNA or housekeeping genes provides identification of those transcripts which are essentially absent in vitro, but are on throughout, or during, various phases of infection.

Having identified potential promoters having on/off characteristics, the promoter region is then cloned upstream of a reporter gene in a vector appropriate for the selected pathogen. By "appropriate" it is meant a vector capable of replicating stably in a selected pathogen. The present invention is based upon the use of expression vector systems which use a promoter that is essentially "off" in vitro and turns "on" selectively during a particular phase of the infection process. By "on" it is meant that the promoter functions in its normal capacity by inducing or promoting expression of the attached gene and that transcription is detectable; by "off" it is meant that the promoter does not function in its normal capacity thus resulting in very little or no detectable transcription. Preservation of the conditional and temporal expression of the promoter, or its "on"/"off" characteristics, within this new construct, during in vitro and in vivo growth, is confirmed visually (luminescence) and by RT-PCR using primers specific to the reporter mRNA. Upon confirmation of the preservation of these characteristics by the promoter, the reporter gene coding region is replaced with a ribozyme or antisense RNA construct for the potential target gene. Determination of the optimal ribozyme or antisense RNA sequence to inhibit target gene expression is first carried out in vitro using a standard controllable promoter such as a T7 promoter coupled with IPTG/lacIPO controlled expression of T7 RNA polymerase.

The expression vector is then introduced into the selected pathogen using standard techniques. Introduction of the vector carrying the ribozyme or antisense RNA construct into the selected pathogen should not affect growth or expression of the target gene in vitro. Introduction of the construct into animal models, however, results in the expression of the ribozyme or antisense RNA construct resulting in a reduction in target gene expression. Levels of gene expression can be monitored by RT-PCR of total RNA isolated from infected tissue at various times during the infection and correlated with rRNA, housekeeping gene or recombinantly introduced marker gene controls and viable cell counts. Reduction in target mRNA is correlated with infection progression including disease pathology, luminescence in thin tissue sections to allow determination of the numbers of metabolically-active pathogens and viable cell counts to prioritize gene targets for development of therapeutic agents. For example, in those cases where a significant reduction in target mRNA, but little effect on viable cell count, is seen, the gene will be considered to be a less attractive target than situations where reduction in viable counts correlates with decreased target mRNA by RT-PCR analysis.

Genes and gene products identified according to the method of the present invention may then be used in the design of therapeutic and diagnostic agents. For example, genes identified in accordance with this method as essential to a selected pathogen in the infection process and proteins encoded thereby may serve as targets for the screening and development of natural or synthetic chemical compounds which have utility as therapeutic drugs for the treatment of infection by this pathogen. As an example, a compound capable of binding to such protein encoded by such gene and inhibiting its biological activity may be useful as a drug component preventing diseases or disorders resulting from the growth of a particular organism. Alternatively, compounds which inhibit expression or reduce expression of an essential gene are also believed to be useful therapeutically.

Conventional assays and techniques may be used for screening and development of such therapeutics. For example, a method for identifying compounds which specifically bind to or inhibit proteins encoded by these gene sequences can include simply the steps of contacting a selected protein or gene product with a test compound to permit binding of the test compound to the protein; and determining the amount of test compound, if any, which is bound to the protein. Such a method may involve the incubation of the test compound and the protein immobilized on a solid support. Still other conventional methods of drug screening can involve employing a suitable computer program to determine compounds having similar or complementary structure to that of the gene product or portions thereof and screening those compounds for competitive binding to the protein. Such compounds may be incorporated into an appropriate therapeutic formulation, alone or in combination with other active ingredients. Methods of formulating such therapeutic compositions, as well as suitable pharmaceutical carriers, and the like are well known to those of skill in the art.

Accordingly, through use of such methods, the present invention is believed to provide compounds capable of interacting with these genes, or encoded proteins or fragments thereof, and either enhancing or decreasing the biological activity, as desired. Such compounds are also encompassed by this invention.

Numerous modifications and variations of the present invention are included in the above-identified specification and are expected to be obvious to one of skill in the art. Such modification and alterations to the compositions and processes of the present invention are believed to be encompassed in the scope of the claims appended hereto.

Each reference disclosed herein is incorporated by reference herein in its entirety. Any patent application to which this application claims priority is also incorporated by reference herein in its entirety.

The following nonlimiting examples are provided to further illustrate the present invention.

EXAMPLES

Example 1: Gene Essentiality

The essentiality of genes expressed in *S. aureus* infections is determined by introduction of $10^2$–$10^8$ cells infected with a selected strain of *S. aureus*, for example, RN4220, into an appropriate animal model such as the murine wound or pyelonephritis models. Infected tissues are recovered from the animals at various times post infection. Total RNA is isolated from the tissues and subjected to RT-PCR directed by primers designed using a S. aureus genome database to amplify all transcripts encoded by the S. aureus strain under study. The promoters of genes whose transcripts are temporally and conditionally controlled are then ligated into an E. coli/S. aureus shuttle vector at the unique HindIII site of pCU1 in accordance with procedures described by Augustin et al., Eur. J. Biochem., 1992, 204:1149–1154. This shuttle vector also carries the reporter gene fusion, luxAB, containing appropriate codons for S. aureus translation inserted in the unique EcoR1 site of pCU1. Recombinants are amplified in E. coli using resistance to ampicillin (100 mg/ml) as a selection.

The recombinant plasmids so generated are then isolated from E. coli and introduced by electroporation into S. aureus RN4220, selecting for chloramphenicol resistance (10 mg/ml) and then transferred into the virulent S. aureus strain WCUH29, or modified to carry the genes for the biosynthesis and recycling of the substrate and fatty acid for the luciferase reaction inserted in the chromosome at a position known to have no effect on virulence. Luciferase expression is determined visually by looking for luminescence in thin tissue sections following exposure to vapors of the aldehyde substrate, dodecanol, of the luminescence reaction or by RT-PCR analysis for luciferase specific mRNA both in vitro and in vivo to confirm whether the characteristics of the promoter have been preserved. If the "on/off" characteristics of the promoter have been preserved, the coding sequence of the luciferase gene is replaced by that of a ribozyme or antisense RNA specific for a candidate gene under study. The new construct is inserted into S. aureus modified to carry the entire luciferase operon optimized for expression in S. aureus in the chromosome, or modified to carry luxAB, which recombinant clone may be exposed to aldehyde to monitor expression. Expression during in vitro growth of the ribozyme or antisense RNA as well as its target RNA is monitored to confirm appropriate expression. The expression of both is then be monitored during infection by growing the S. aureus carrying the constructs in the presence of antibiotic overnight and introducing $10^2$–$10^8$ viable cell counts into the animal model. Reduction in target mRNA is correlated with infection progression including disease pathology, luminescence in thin tissue sections to allow determination of the numbers of metabolically-active bacteria and viable cell counts so that gene candidates can be prioritized for development of therapeutic agents.

Example 2: *Staphylococcus aureus* Promoter that is "on" in an in vivo Model

A S. aureus promoter sequence is provided as an exemplifcation of a promoter that may be modulated in "on" and "off" modes of expression. This promoter sequence for the open reading frame (herein "ORF") is transcribed in vivo in animal models of infection, but not in vitro. This promoter may be used in the methods of the invention.

There are two preferred putative promoter sequence regions indicated with underlining. Sequences in SEQ ID NO:1 (below) that are underscored and in bold indicates the most preferred putative promoter region. Upstream of this is a second preferred putative promoter region (underscored only). The ATG start codon of the gene transcribed from the sequence of SEQ ID NO:1 is italicized. Genes to be tested in the methods described herein may be expressibly ligated to the promoter sequence including or excluding this start codon.

```
5'-GATGCAGAAGCGATTTACACGTACGAAGGT                                        [SEQ ID NO:1]

ACACATGAAATTAATGCCTTAGTAATTGGACGCGCTTTGACTGGAGATTCTGCTTTCGTATAAATAGC

AAATAATTATATGAGATGCATTAATTTCACTAAAAAAGACTTATTTTAAGCATAAAGCTTTTTCCTTA

AATAAGAGGCTAAGATGACTGTCAAAGATACTTAATTAATTTTATAAAATAGCAACGTTATTCCAATT

ATCTTAATGGTTATCTTATCCTCAACTAAATTGGAGGAATCACTATG . . .3'
```

What is claimed is:

1. A method of determining gene essentiality in a selected pathogen comprising:
    (a) preparing an expression vector comprising a promoter of a gene having on/off characteristics and a reporter gene;
    (b) expressibly linking the promoter in the expression vector with a ribozyme or antisense construct for a potential target gene;
    (c) introducing the expression vector containing the ribozyme or antisense construct into a selected pathogen;
    (d) infecting at least one animal with the pathogen containing the expression vector;
    (e) determining gene expression levels of the target gene; and
    (f) correlating target gene expression levels with progression of the infection in the animal to identify genes essential to growth of the selected pathogen.

2. The method of claim 1 wherein the selected pathogen is selected from the group consisting of Streptococcus, *Streptococcus pneumoniae*, Staphylococcus, *Staphylococcus aureus*, Enterococcus, *Enterococcus faecalis*, Pseudomonas, *Pseudomonas aeruginosa*, Escherichia, and *Escherichia coli*.

3. The method of claim 1 wherein the animal of the infecting step is selected from the group consisting of a rodent, a mouse, a rat, a rabbit, and a guinea pig.

4. A method of determining gene essentiality in a selected pathogen comprising:
    (a) preparing an expression vector comprising a promoter of a gene having on/off characteristics and a reporter gene;
    (b) expressibly linking the promoter in the expression vector with a ribozyme or antisense construct for a potential target gene;
    (c) introducing the expression vector containing the ribozyme or antisense construct into a selected pathogen;
    (d) infecting at least one animal with the pathogen containing the expression vector;
    (e) determining levels of mRNA of the target gene; and
    (f) correlating levels of mRNA with progression of the infection in the animal to identify genes essential to growth of the selected pathogen.

5. The method of claim 4 wherein the selected pathogen is selected from the group consisting of Streptococcus, *Streptococcus pneumoniae*, Staphylococcus, *Staphylococcus aureus*, Enterococcus, *Enterococcus faecalis*, Pseudomonas, *Pseudomonas aeruginosa*, Escherichia, and *Escherichia coli*.

6. The method of claim 4 wherein the animal of the infecting step is selected from the group consisting of a rodent, a mouse, a rat, a rabbit, and a guinea pig.

7. A method of determining gene essentiality in a selected pathogen comprising:
    (a) identifying a potential target gene;
    (b) preparing an expression vector comprising a promoter of a gene having on/off characteristics and a reporter gene;
    (c) confirming that the on/off characteristics of the promoter in the expression vector are preserved;
    (d) replacing the reporter gene in the expression vector with a ribozyme or antisense construct for the potential target gene;
    (e) introducing the expression vector containing the ribozyme or antisense construct into a selected pathogen;
    (f) infecting at least one animal with the pathogen containing the expression vector;
    (g) determining levels of mRNA of the target gene; and
    (h) correlating levels of mRNA with progression of the infection in the animal to identify genes essential to growth of the selected pathogen.

8. The method of claim 7 wherein the selected pathogen is selected from the group consisting of Streptococcus, *Streptococcus pneumoniae*, Staphylococcus, *Staphylococcus aureus*, Enterococcus, *Enterococcus faecalis*, Pseudomonas, *Pseudomonas aeruginosa*, Escherichia, and *Escherichia coli*.

9. The method of claim 7 wherein the animal of the infecting step is selected from the group consisting of a rodent, a mouse, a rat, a rabbit, and a guinea pig.

10. A method of determining gene essentiality in a selected pathogen comprising:
    (a) preparing an expression vector comprising a promoter of a gene having on/off characteristics and a reporter gene;
    (b) expressibly linking the promoter in the expression vector with a ribozyme or antisense construct for a potential target gene;
    (c) introducing the expression vector containing the ribozyme or antisense construct into a selected pathogen;
    (d) infecting at least one animal with the pathogen containing the expression vector;
    (e) determining levels of protein expressed by the target gene; and
    (f) correlating levels of protein with progression of the infection in the animal to identify genes and gene products essential to growth of the selected pathogen.

11. The method of claim 10 wherein the selected pathogen is selected from the group consisting of Streptococcus, *Streptococcus pneumoniae*, Staphylococcus, *Staphylococcus aureus*, Enterococcus, *Enterococcus faecalis*, Pseudomonas, *Pseudomonas aeruginosa*, Escherichia, and *Escherichia coli*.

12. The method of claim 10 wherein the animal of the infecting step is selected from the group consisting of a rodent, a mouse, a rat, a rabbit, and a guinea pig.

13. A kit comprising a vector comprising a promoter of SEQ ID NO:1 and a reporter gene.

14. A vector comprising a promoter of SEQ ID NO:1 and a reporter gene.

15. A pathogen comprising a vector comprising a promoter of SEQ ID NO:1.

16. An expression vector comprising a promoter of SEQ ID NO:1 and a reporter gene.

17. A pathogen comprising an expression vector comprising a promoter of SEQ ID NO:1 and a reporter gene.

18. A method of determining gene essentiality in a selected pathogen comprising:
    (a) preparing an expression vector comprising a promoter of a gene having on/off characteristics and a reporter gene;
    (b) expressibly linking the promoter in the expression vector with a ribozyme or antisense construct for a potential target gene;
    (c) introducing the expression vector comprising the ribozyme or antisense construct into a selected pathogen;

(d) infecting at least one animal with the pathogen comprising the expression vector; and (e) determining if the target gene is essential to growth of the selected pathogen.

19. The method of claim 18 wherein the selected pathogen is selected from the group consisting of Streptococcus, *Streptococcus pneumoniae*, Staphylococcus, *Staphylococcus aureus*, Enterococcus, *Enterococcus faecalis*, Pseudomonas, *Pseudomonas aeruginosa*, Escherichia, and *Escherichia coli*.

20. The method of claim 18 wherein the animal of the infecting step is selected from the group consisting of a rodent, a mouse, a rat, a rabbit, and a guinea pig.

21. A method of determining gene essentiality in a selected pathogen comprising:

(a) preparing an expression vector comprising a promoter of a gene having on/off characteristics and a reporter gene;

(b) expressibly linking a the promoter in the expression vector with a ribozyme or antisense construct for a potential target gene;

(c) introducing the expression vector comprising the ribozyme or antisense construct into a selected pathogen;

(d) infecting at least one animal with the pathogen comprising the expression vector; and (e) determining cell viability.

22. The method of claim 21 wherein the selected pathogen is selected from the group consisting of Streptococcus, *Streptococcus pneumoniae*, Staphylococcus, *Staphylococcus aureus*, Enterococcus, *Enterococcus faecalis*, Pseudomonas, *Pseudomonas aeruginosa*, Escherichia, and *Escherichia coli*.

23. The method of claim 21 wherein the animal of the infecting step is selected from the group consisting of a rodent, a mouse, a rat, a rabbit, and a guinea pig.

24. A method of determining gene essentiality in a selected pathogen comprising:

(a) preparing an expression vector comprising a promoter of a gene having on/off characteristics and a reporter gene;

(b) expressibly linking the promoter in the expression vector with a ribozyme or antisense construct for a potential target gene;

(c) introducing the expression vector comprising the ribozyme or antisense construct into a selected pathogen;

(d) infecting at least one animal with the pathogen comprising the expression vector;

(e) determining cell viability; and (f) correlating cell viability with progression of the infection in the animal to identify genes and gene products essential to growth of the selected pathogen.

25. The method of claim 24 wherein the selected pathogen is selected from the group consisting of Streptococcus, *Streptococcus pneumoniae*, Staphylococcus, *Staphylococcus aureus*, Enterococcus, *Enterococcus faecalis*, Pseudomonas, *Pseudomonas aeruginosa*, Escherichia, and *Escherichia coli*.

26. The method of claim 24 wherein the animal of the infecting step is selected from the group consisting of a rodent, a mouse, a rat, a rabbit, and a guinea pig.

* * * * *